United States Patent
Voigt et al.

(10) Patent No.: US 7,590,617 B1
(45) Date of Patent: Sep. 15, 2009

(54) SYSTEM PROVIDING DESKTOP INTEGRATION OF PATIENT INFORMATION AND DOCUMENT MANAGEMENT

(75) Inventors: Christopher Thomas Voigt, McLean, VA (US); Scott Allen Raimist, Centreville, VA (US)

(73) Assignee: American Management Systems, Incorporated, Fairfax, VA (US)

( * ) Notice: Subject to any disclaimer, the term of this patent is extended or adjusted under 35 U.S.C. 154(b) by 0 days.

(21) Appl. No.: 09/366,749

(22) Filed: Aug. 4, 1999

(51) Int. Cl.
G06F 7/00 (2006.01)
G06F 3/00 (2006.01)
G06F 17/00 (2006.01)

(52) U.S. Cl. .......................... 707/3; 719/328
(58) Field of Classification Search ............... 705/1, 705/2, 3, 4, 1.2; 707/100–103 Z, 3, 10; 709/328; 719/328–329
See application file for complete search history.

(56) References Cited

U.S. PATENT DOCUMENTS

| | | | | |
|---|---|---|---|---|
| 5,644,764 A | * | 7/1997 | Johnson et al. | 707/103 |
| 5,668,998 A | * | 9/1997 | Mason et al. | 709/328 |
| 5,832,450 A | * | 11/1998 | Myers et al. | 705/3 |
| 5,946,659 A | * | 8/1999 | Lancelot et al. | 705/3 |
| 6,067,547 A | * | 5/2000 | Douceur | 707/100 |
| 6,163,781 A | * | 12/2000 | Wess, Jr. | 705/2 |
| 6,168,563 B1 | * | 1/2001 | Brown | 705/2 |
| 6,260,021 B1 | | 7/2001 | Wong et al. | |
| 6,385,589 B1 | * | 5/2002 | Trusheim et al. | 705/2 |
| 6,401,138 B1 | * | 6/2002 | Judge et al. | 709/328 |

OTHER PUBLICATIONS

American Management Systems, Inc., "Document Imaging and Work Flow Software for Health Information Management", 1995.
American Management Systems, Inc., "Document Imaging and Work Flow Software for Patient Information Management", 1996.
American Management Systems, Inc., "HRLink Increases Productivity and Effectiveness", 1998.
American Management Systems, Inc., "Enabling Health Systems to Thrive in Tomorrow's Environment", 1998.

* cited by examiner

Primary Examiner—Sam Rimell
(74) Attorney, Agent, or Firm—Staas & Halsey LLP

(57) ABSTRACT

A desk top system patient information management system includes an integration interface for an existing healthcare system that provides access to a separate and existing document management system. The integration interface provides modifications (added controls) for a user interface of the healthcare system that allow a user to initiate access to the document management system. The controls include controls for making a query for a document such as a chart or patient notes and for modifying the document. The integration interface also includes objects (methods and data) that perform the access to the document management system based on the information of the user interface and provide the information requested to the interface for viewing and modification.

9 Claims, 12 Drawing Sheets

SYSTEM PROVIDING DESKTOP INTEGRATION OF PATIENT INFORMATION AND DOCUMENT MANAGEMENT

BACKGROUND OF THE INVENTION

1. Field of the Invention

The present invention is directed to a desktop system that integrates an existing healthcare application with a separate document management system and, more particularly, to a system that includes an integration interface that modifies a user interface of the healthcare application and includes objects that access the document management system using information from the user interface.

2. Description of the Related Art

Healthcare workers depend on viewing patient records to complete their work. Oftentimes paper documents are used, but many organizations have made use of electronic document imaging and management. The benefits of electronic document management are great—concurrent document access, permanent storage and retrieval, workflow capabilities, etc. But a document imaging application may add to the already long list of systems that a healthcare organization might already use.

The healthcare computing environment consists of many separate and diverse systems. Frequently healthcare workers must utilize a number of different systems to complete their work. The effort needed for the worker to move between these systems has a negative impact on their productivity and widens the opportunity for errors. Effort is wasted administering and maintaining separate security profiles across these many systems.

The traditional method for implementing patient document management systems is to add a new application along side existing applications. This is not ideal. Typical systems that are added alongside existing healthcare applications are the American Management System AccountLink and RecordLink®, which provide account and record functionality for healthcare business office and medical records offices, respectively. These existing AMS systems are used side-by-side with existing healthcare applications. The LanVision ChartVision™ (see www.lanvision.com) and the MedPlus ChartMaxx™ (see www.medplus.com) are also complete document imaging systems that are run alongside other healthcare applications.

What is needed is a system that facilitates a tight integration of document management into existing healthcare applications.

SUMMARY OF THE INVENTION

It is an object of the present invention provide integration of document management into existing healthcare applications by providing an integration application programming interface (API).

It is another object of the present invention to minimize the effort needed to move between these different applications.

It is an additional object of the present invention to reduce the labor involved in maintaining and accessing separate systems.

It is another object of the present invention to improve security, user authorization, user authentication, patient chart deficiency processing and auditing.

It is also an object of the present invention provide a healthcare specific document imaging application program interface (API) that can easily be integrated into an existing healthcare application.

It is a further object of the present invention to provide an API that allows simple and direct access to a typical separate patient document management system.

The above objects can be attained by a system that has an integration interface for an existing healthcare system that provides access to a separate and existing document management system. The integration interface provides modifications (added controls) for a user interface of the healthcare system that allow a user to initiate access to the document management system. The integration interface also includes objects (methods and data) that perform the access to the document management system based on the information of the user interface and provides the information requested to the interface for viewing and modification.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Healthcare workers make use of different computer applications to accomplish their tasks. Physicians may use a clinical hospital information system to access their patient's demographic information while retrieving laboratory results from another system and transcribing a diagnosis into yet another. Likewise, someone in a patient accounting role may access a billing system, the main hospital information system, and a collection application.

Figure 1:
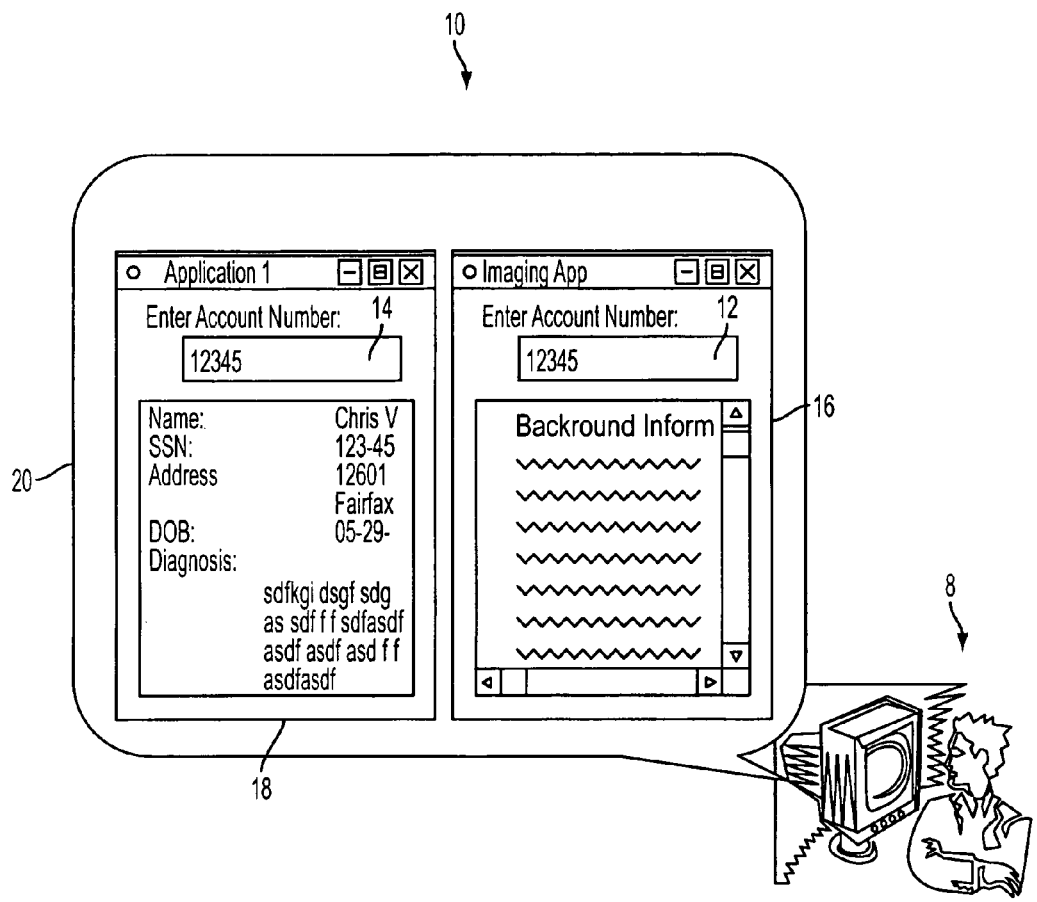
FIG. 1 illustrates a non-integrated interface of two separate systems.

If a healthcare organization implements a document management system, it is typically added as a separate application on the user's desktop. The addition of a document imaging system adds another level of complexity to the user's work. As illustrated in FIG. 1, the user 8, such as a doctor, in using a conventional system 10, for example, enters the same account number into two different entry spaces 12 and 14 in two different windows (user interfaces) 16 and 18 appearing on single display 20 of the computer 22. To move between the systems requires that the user 8 change interfaces and enter some of the same identifying information twice.

The present invention minimizes the effort needed to move between the applications and presents a unified application front end to the user. The present invention provides a mechanism to integrate document management features into an existing healthcare system.

Figure 2:
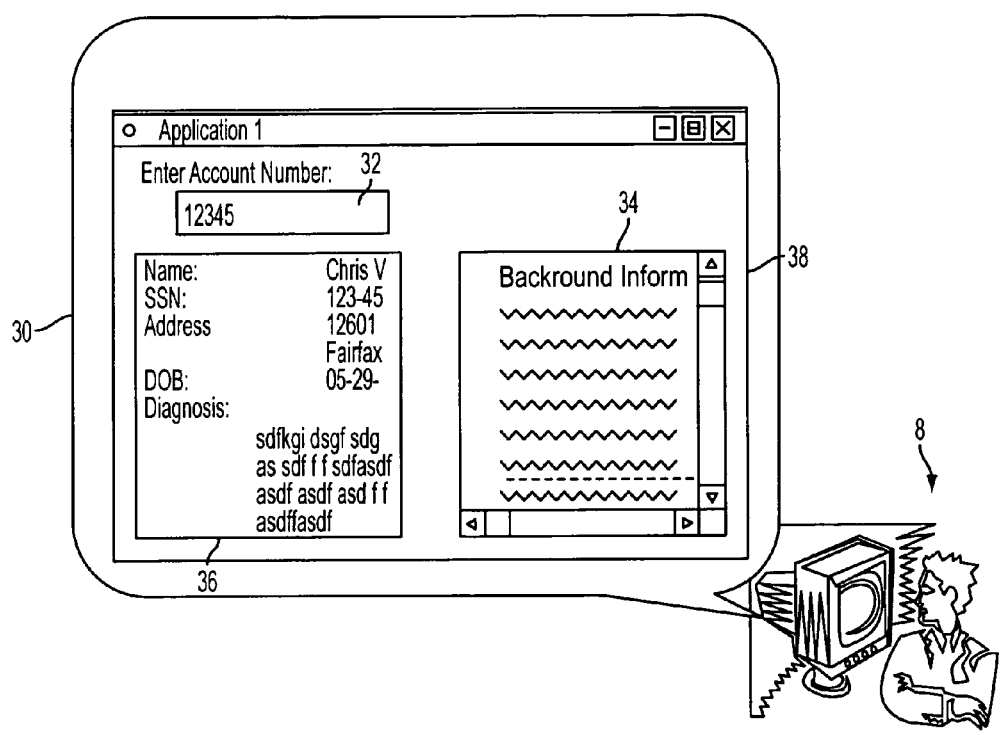
FIG. 2 depicts an integrated interface for two separate systems according to the present invention.

Using this mechanism, a document management system provides a concise set of programmable interfaces to its application features and functions. An existing healthcare application hooks the document management system into it's own user interface. FIG. 2 depicts an interface in which a single set of information provides access to the information in two separate systems. As can be seen, the user 8 is presented with a display 30 in which only a single entry space 32 is provided and the information is presented by two viewers 34 and 36 from two different systems in the same window 38.

The programmable interface provided by the document management system includes all functions that are required by a document management system. These typically include: logon, locate a document, display a document, navigate through pages of a document, add notations to a document, process deficiencies for a patient's chart, print a document and logoff.

Figure 3:
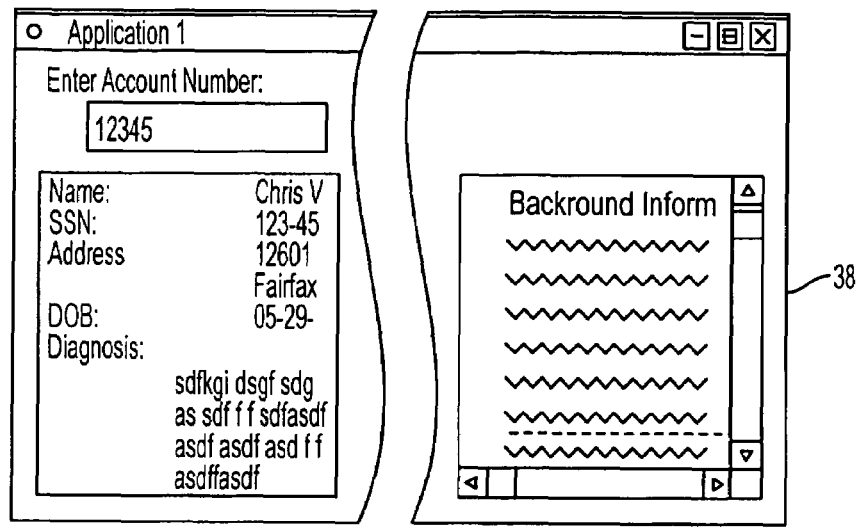
FIG. 3 illustrates interaction in a system according to the present invention.
Figure 3:
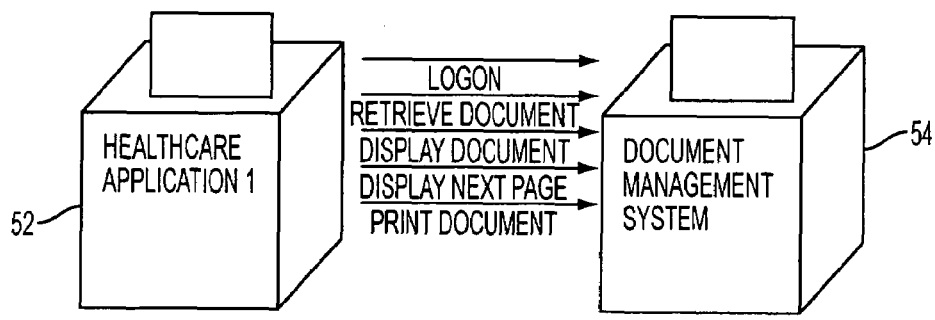

FIG. 3 illustrates how the programmable interface of the present invention is used by a healthcare application to control the display of patient documents. System logons and security administration is simplified for both users and system administrators. A single sign-on and security validation is performed. The healthcare application 52 performs the initial logon for the user and validates their security privileges. The document management system 54 depends on the main healthcare application 52 for valid authorization and authentication of the user and the logon to the system 54 is performed for the application 52. User error is also minimized. Key information used to retrieve patient documents in the document management system 54 is provided directly for the main healthcare application 52. The user does not need to re-key this data to view the patient documents. This virtually eliminates the possibility of retrieving and viewing the wrong patient's documents. A simplified user work environment is also provided. The end users see a single integrated application on the screen. This minimizes the amount of application switching required to perform the work. Under the integrated application paradigm, it is easier to train and support users.

Figure 4:
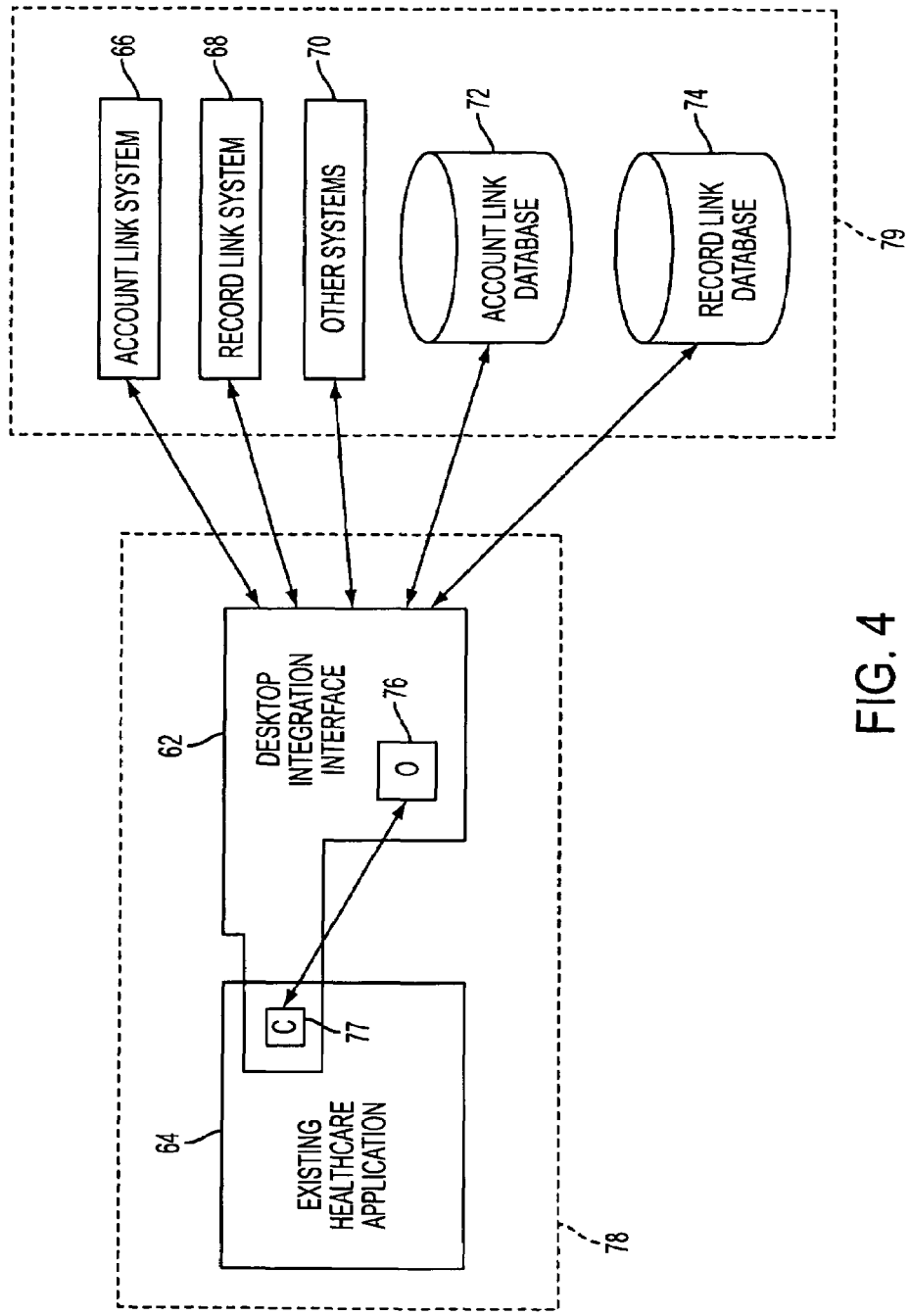
FIG. 4 depicts the architecture of a system according to the present invention.

The interface 62 of the present invention, as depicted in FIG. 4, integrates an existing health care application 64 with one or more existing Patient Documents Management Systems (PDMS) 66, 68 and 70, and databases 72 and 74. The interface 62 includes objects 76 and controls 77 where the controls 77 are actually made a part of the healthcare application 64 as depicted by the portion of the interface 62 that overlaps with the application 64 in FIG. 4. The objects can be implemented in C++ but are preferably implemented as Microsoft ActiveX Objects and are generally not visible to end-users whereas the controls are preferably ActiveX Controls (buttons, editable fields, viewers, etc.) and are visible components on an end-user's screen with which they may interact. For example, an object may contain security information about which documents a particular user may access, but a control would be used to display those documents to the user. The controls contain standard window attributes such as background color, font, text color, frame style, display formats, 3D effects to achieve this seamless appearance.

Figure 5:
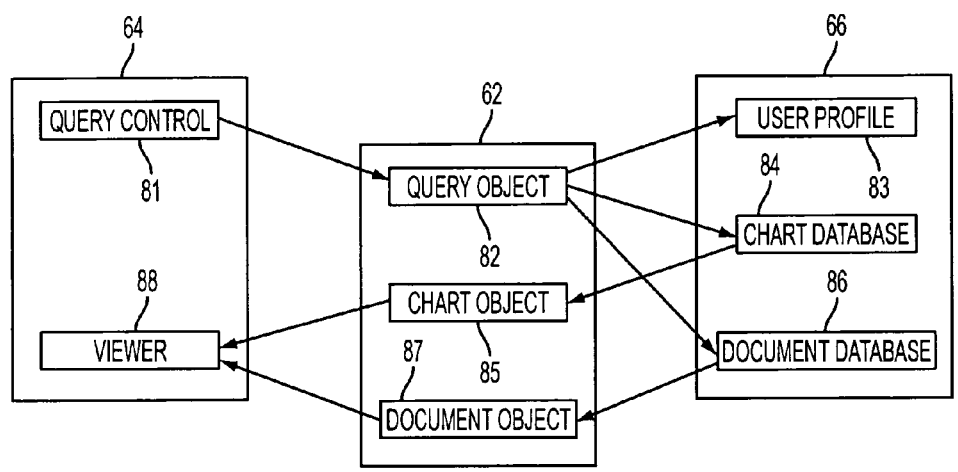
FIG. 5 illustrates a query.

During a typical interaction, a user of the application 64 requests a patient chart by clicking a document button (for a chart document, a text document, and image document, voice document, spread sheet document, audio, video, etc.) or control 81 (see FIG. 5) added to a user interface (window) in the application 64. The control would initiate a query object 82 within the integration interface 62 which accesses a user profile 83 in an existing document management system 66 for user information to authenticate that the user can access system 66. Using the patients information entered into the application 64 via the user interface, the query object 82 accesses the chart database 84 to obtain the patients chart from the document management system, 66 and the chart would be provided to a chart object 85. A document database 86 is also accessed to obtain documents associated with the chart which are provided to a document object 87. The chart object 85 and document object 87 presents chart and document to the user through a viewer 88 of the application 64 where it is displayed to the user. The user would be able to use other controls to modify the chart and/or document through modify controls and modify objects.

The integration interface 62 can be implemented on the same desktop workstation computer 78 as the application 64 as depicted by the dashed line of FIG. 4 while the document management systems can be implemented on a single mainframe computer 79. Other configurations may be preferable in certain situations. For example, the application 64 and the controls of the interface 62 could be implemented on a single desktop work station while the objects are implemented on an object server computer and the management systems along with the database systems are each implemented on different document server computers. The application, interface, management systems and database systems could also be implemented on a single machine. Additionally, the processes of the invention can be stored and distributed on a storage medium such as a magnetic disk or CD and distributed over a network such as the Internet.

The integration interface 62 of the invention typically has several objects and controls which include: a Session Manager Object, a Query Object, a Chart Object, a Chart Control, a Document Object, a Document Display Control and an Image Display Control. Each of these objects and controls will be discussed in more detail hereinafter and pseudocode for such is provided in the attached Appendix.

The Session Manager object retains information about the current work session. This information drives the way in which other objects function. For example, if the user is not a physician, the user will not be able to use the Complete function in the Deficiency object to complete chart deficiencies.

The Session Manager object has attributes which include the UserName which is the full name of the currently logged on user and is blank if a user is not logged on. The UserID is also included and is the identifier (ID) of the currently logged on user and is blank if a user is not logged on. A UserRole attribute is provided which is the role of the currently logged on user, such as physician, nurse, administrator, etc. The role is preferably kept in a look up table which provides information about the access and security privileges of a user. For example, an attending doctor may have a role of "Physician" which allows the doctor to view charts, complete chart deficiencies, and dictate transcribed documents. The "Physician" role would not allow the doctor to run system administrator programs such as table maintenance. Another attribute is LogonTime which is the time that the currently logged on user started this session. A UserPreferences attribute is also provided and is a collection of properties that control preferences of various other interface 62 objects/controls, such as default print device. The user preferences can be provided in a look-up table referenced by user name.

The Session Manager object has methods which include a Logon method which logs onto the Patient Document Management system and other external image storage systems, checks to determine whether the user has a valid ID and loads a user preferences table. The Logon method also loads the role table and sets the logon time.

A Logoff method in the Session Manager object logs the current user out of the Patient Document Management system and logs the user out of any other sessions initiated during the logon method call, releases resources and deletes cached objects.

An AuditEvent method writes information about an event to a central audit log.

The session manager methods also include a CheckPermission permission method which checks an interface permission table to see if the current user has privileges to perform the requested action. For example, using the Image Display control, a user may not have privileges to view highly confidential or HIV test result document types. Actions, data, and permissions in the Permission table are typically configured by system administrators.

A Query object is used to locate charts or types of documents within the document management system. The results of a given query are used to determine which documents are displayed by the Display control. The Query object may return Chart or Document objects.

Query object attributes include KeyQueryFields which is a list of fields that may be used to query the Patient Document Management System (PDMS—66, 68, 70, 72 or 74). These fields may be used as keys in a query (i.e. the data for these fields is indexed in the database to enhance query performance). The Query object retrieves the possible Key query fields from the target PDMS when the object is instantiated. The attributes also include a FilterQueryFields which is a list of fields that may be used to query the existing Patient Document Management System. The Query object retrieves the possible Filter query fields from the PDMS when the object is instantiated. A DocumentTypes attribute is a list of document types that may be used to query the Patient Document Management System. These document types may be specified in a document query to target a particular group of documents (e.g. Nursing Report or Remittance). The Query object retrieves the possible DocumentTypes from the PDMS when the object is instantiated. A ChartTypes attributes provides a list of patient chart types that may be used to query the Patient Document Management System. These chart types may be specified in a chart query to target a particular group of charts (e.g. Medical Record or Patient Accounting charts). The Query object retrieves the possible ChartTypes from the PDMS when the object is instantiated.

Query Object methods include several different methods.

A QueryForCharts method queries the Patient Document Management System for charts using specified key and filter fields. This method returns a collection of one or more chart objects. The query may be limited to return only n chart objects and a ContinueQuery method may be used to retrieve more charts that match the query criteria. The charts query uses a key and a filter to produce a conventional query suitable for a conventional chart management system. The returned chart is displayed in a viewer of the application user interface window using conventional window display techniques. If additional charts are available, a button (not shown) on the user interface allows the selection of more charts where the ContinueQuery method is executed using a query number for the subsequent calls.

A QueryForDocuments method queries the Patient Document Management System for documents using specified key and filter fields. This method returns a collection of one or more document objects. The query may be limited to return only n document objects and the ContinueQuery method may be used to retrieve more documents that match the query criteria. A key and filter derived are used as query criteria to obtain the desired documents. Again the query is a conventional query used to query a conventional document management system to obtain documents that match the criteria.

The ContinueQuery method continues a query started with either QueryForCharts or QueryForDocuments. This method returns more charts or documents from the database that match the previously specified query criteria. The ContinueQuery functionality follows conventional query continuation used to query a conventional document management system.

A CancelQuery method cancels a query started with either QueryForCharts or QueryForDocuments using a conventional resource release technique suitable for the particular system being queried.

Figure 6:
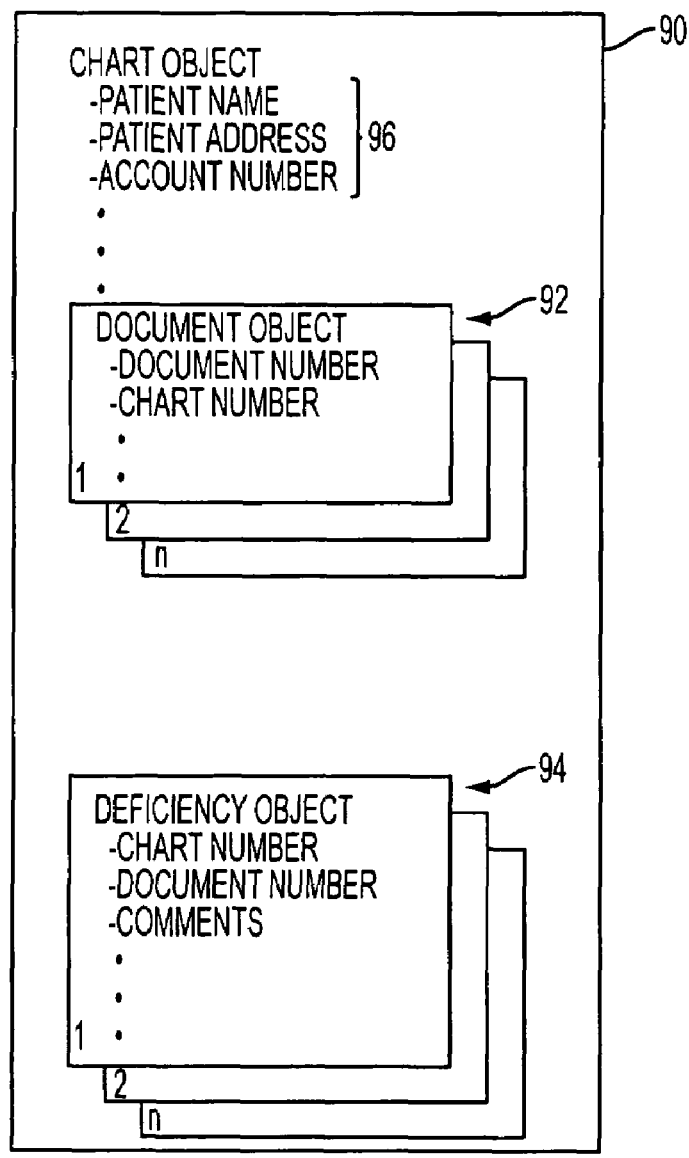
FIG. 6 illustrates object relationships.

The Chart object is used to access charts within the document management system. It may be used to modify or delete existing charts, change the attributes of charts, or to print charts. The Chart Object 90 contains a collection of both Document objects 92 and Deficiency objects 94. FIG. 6 illustrates this object containment.

The Chart Object attributes include ChartDocuments (a collection of Document objects 92) which is a collection of all of the documents that the chart contains. Each of the documents is assigned a document number. A ChartDeficiencies (a collection of Deficiency objects 94) attribute is a collection of all of the deficiencies that the chart contains. This includes chart level deficiencies (e.g. a certain document does not exist in this chart) as well as document level deficiencies (e.g. a given document is missing a signature). A Chart Number attribute is provided which is the unique identifier for this chart. A ChartType attribute is the type of the chart (e.g. Patient Account or Medical Record). Chart demographic attributes 96 are also provided and include Patient Name, Patient Address, Account Number, Financial Class, Patient Type, etc. and which are general chart attributes from the existing PDMS database.

The Chart Object includes several methods used to output and change charts.

A PrintChart method prints information about the chart to a default or specified printer either of the existing application or the document management system and where the printing can be to a printing server. The method also prints the chart's documents and triggers an audit event. It is frequently necessary to audit whenever a user prints any part of a medical record, among other things. The audit record is input into a conventional audit database for later reference and reporting.

A FaxChart method sends information about the chart to a default or specified facsimile machine using a telephone number specified. The facsimile machine can be a facsimile server. Like the print chart method this method also sends the chart's documents to the facsimile machine and triggers an audit event.

An UpdateChart method updates chart attributes. The interface 62 performs the necessary database field updates in the PDMS using conventional update techniques for a conventional management system such as previously mentioned.

A MergeChart method merges two charts together in the PDMS. Again conventional techniques are used to merge the charts in the PDMS.

A DeleteChart method removes a chart from PDMS using conventional chart deletion techniques. The chart is removed from the users ability to access it but is archived.

An AddDocument method adds a document to the chart of the object using conventional techniques and the document number.

A RemoveDocument method removes a document from this chart using the document number and conventional techniques.

Figure 7:
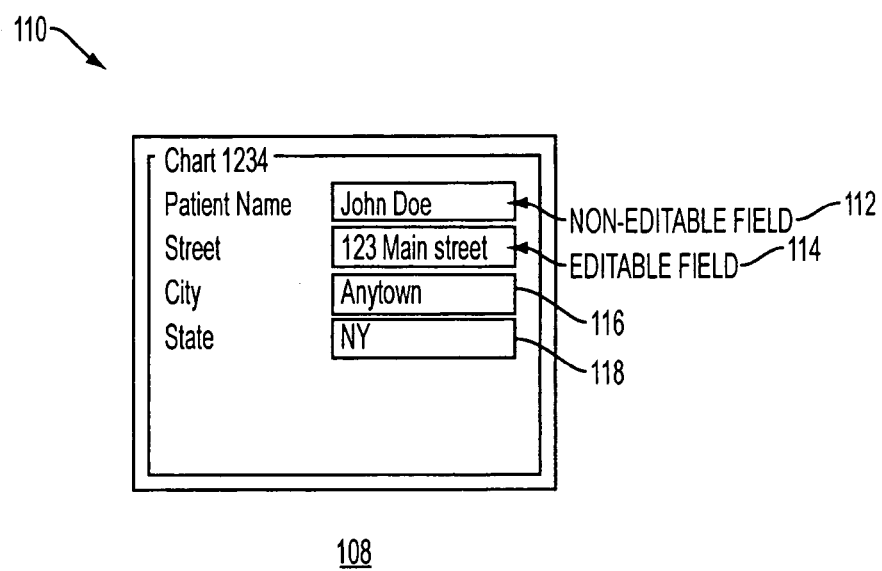
FIG. 7 illustrates a chart control.

The Chart Display control visual interface 108, as depicted in FIG. 7, conventionally displays the attributes of a chart (e.g. Patient Type, Financial Class, Chart Status) in display fields. FIG. 7 particularly shows the chart number 110 and has display fields including patient name 112, and address 114, 116 and 118. Some of these fields such as fields 114, 116 and 118 may be edited on the screen. Exactly which fields are display only or editable is configurable. By default, the control conventionally only allows display of fields that the current user's security permits them to view. Likewise, the user's security dictates which fields may possibly be edited.

Chart Display Control attributes include CurrentChart which is a reference (or pointer) to the Chart object that is to be displayed in this control. A DisplayFields attribute specifies which Chart object fields should be displayed in the Chart Display Control's user interface. This is used to limit which fields are viewed beyond the user's basic security permissions. Note that this field allows the embedding application 64 to manipulate the visual presentation of data in this visual control. An EditableFields attribute specifies which Chart object fields may be edited in the Chart Display Control's user interface. This is used to limit which fields can be edited beyond the user's basic security permissions. Each field in EditableFields must be specified in DisplayFields (i.e. a field must be displayed in order for it to be editable). Note that this field also allows the embedding application to manipulate the visual presentation of data in this visual control. The chart display control attributes also include a Visible attribute which specifies whether the control is visible on the screen. Conventional windows attributes are also provided such as BackgroundColor ForegroundColor, Height, Width, etc). These attributes allow the embedding application to manipulate the visual presentation of data in this visual control.

The Chart Display Control includes several methods that allow the modification of fields and the refresh of the display.

The Initialize method of the chart display control conventionally sets up the control for use by conventionally creating the visual controls for each of the DisplayFields specified. Visual controls for each field specified in EditableFields is set for editing and all others are set as read-only.

The Refresh method conventionally refreshes the user interface with data values from the chart referenced by CurrentChart.

The Chart Display Control includes a FieldModified event which signals the owner window when the contents of a field have been changed. When this event is triggered, the owner window would typically invoke the UpdateChart method of the current chart. The field name and field value are passed to the update method.

The Document Object is used to access documents within the document management system. It may be used to modify or delete existing documents, change the attributes of documents, or to print and fax individual documents.

The Document Object has a number of different attributes some of which are required and some of which are optional. A DocumentNumber is a required attribute which is a unique identifier that identifies this document in the PDMS. A ChartNumber attribute, also a required attribute, is an identifier of the chart that contains this document. A Chart attribute is a reference to the chart object that contains this document. If this document's chart has not been retrieved during a session, this may be null. The DocumentType attribute indicates the basic type of the document (e.g. Nursing Note, X-Ray, Physician Order, etc.). Some preferences and access privileges are based on the DocumentType of documents. A NumberOfPages attribute indicates the number of pages this document includes. A Deficiencies attribute is a collection of document deficiencies that this document has. See the Deficiency object for more details. The attributes also include document demographic attributes like EntryDate, ArchiveStatus, etc. where these attributes fields provide further information about the document from the PDMS.

The Document Object includes methods which allow a document to be output and updated and which are similar to the methods of the Chart Objects and which also use conventional techniques. A PrintDocument method prints this document to the default or specified printer and triggers an audit event. A FaxDocument method sends this document to the default or specified fax device and triggers an audit event. An UpdateDocument method updates attributes for this document. For some attributes, the interface 62 will perform the necessary database update in the PDMS. A DeleteDocument method removes the document from the chart and PDMS.

Figure 8:
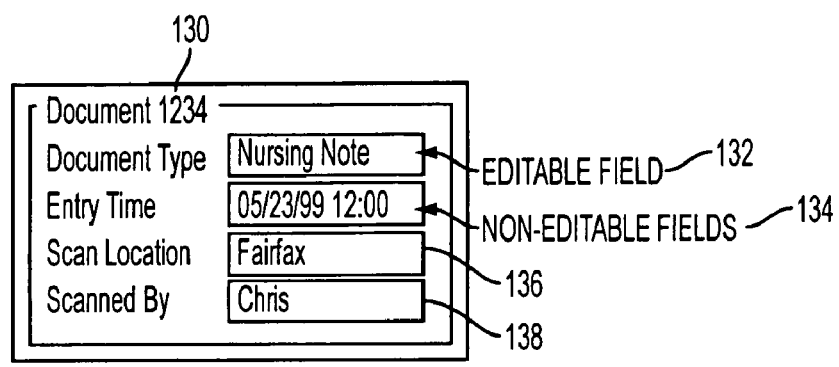
FIG. 8 depicts a document control.

The Document Display control visual interface 128, as depicted in FIG. 8, displays the attributes of a document (e.g. Document Type, Entry Date). In particular, FIG. 8 shows the interface displaying the document number 130 and display fields for document type 132, entry time 134, scan location 136 and who the document was scanned by 138. Some of these fields, such as field 132, may be edited on the screen. Exactly which fields are displayed or editable is configurable. Note that this control does not display the actual image of the given document. The ImageDisplay control of FIG. 9 displays the image while the DocumentDisplay control shows the index values of a specific document. By default, the control only allows display of fields that the current user's security permits them to view. Likewise, the user's security dictates which fields may possibly be edited.

Document Display Control has attributes which include a CurrentDocument attribute which is a reference to the Document object that is to be displayed for this control. A DisplayFields attribute specifies which Document object fields should be displayed in the Document Display Control's user interface 128. This may be used to limit which fields may be viewed beyond the user's basic security permissions. Note that this field allows the embedding application 64 to manipulate the visual presentation of data in this visual control. An EditableFields attribute specifies which Document object fields may be edited in the Document Display Control's user interface. This may also be used to limit which fields may be edited beyond the user's basic security permissions. Each field in EditableFields is specified in DisplayFields (i.e. a field must be displayed in order for it to be editable). Note that this field also allows the embedding application to manipulate the visual presentation of data in this visual control. A Visible attribute specifies whether the control is visible on the screen. Conventional windows attributes are also included such as BackgroundColor, ForegroundColor, Height, Width, etc.)

Document Display Control methods are similar to those provided for chart display control and include an Initialize method which conventionally sets up the control for use by creating the visual controls for each of the DisplayFields specified. Visual controls for each field specified in EditableFields are set for editing and all others are read-only. A Refresh method conventionally refreshes the user interface 128 with data values from the document referenced by CurrentDocument. Document Display Control events include a FieldModified event which signals the owner window when the contents of a field have been changed. When this event is triggered, the owner window typically invokes the UpdateDocument method of the current document.

Figure 9:
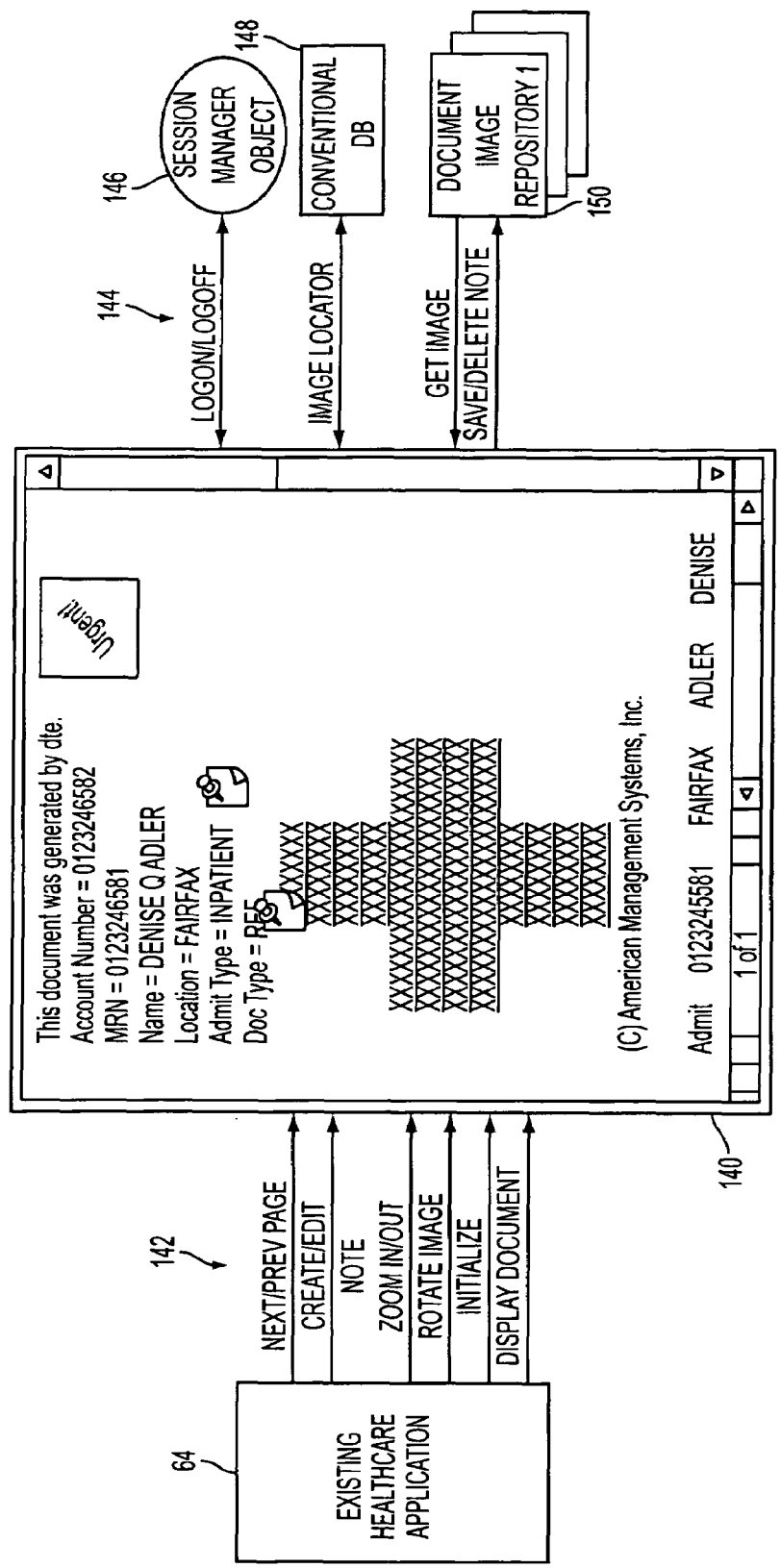
FIG. 9 shows a document viewer.

The Image Display control conventionally displays the actual image view of one or more documents in a user interface or viewer, such as depicted in FIG. 9. This control offers typical image viewing, navigation, and markup functionality. The control also handles acquiring the image from more than one server location or platform (further increasing the scope of integration). As previously discussed, the requirements and design of the Image Display control can be implemented using a conventional technology such as the ActiveX controls available from Microsoft. As another example, FIG. 9 illustrates how the Panagon Image Viewer control available from FileNET of Costa Mesa, Calif. could be used to display a document image. FIG. 9 also depicts the interactions of the control with the existing healthcare application 64 and with the components of the patient document management system. The display control 140 receives commands 142, such as a Next Page command, and performs operations 144 with the components of the document management system, such as the session manager 146, the database 148 and the document repositories 150 such as obtaining an image.

Image Display Control attributes include a DisplayButtons attribute which specifies the toolbar buttons to display in control. Conventional display attributes such as Display Mode, Display Size, Zoom Factor, Brightness, Contrast, etc. are also provided and are set by the embedding application 64.

Image Display Control methods include an Initialize method which conventionally configures the conventional display control. Configuration can include establishing a link to an image server, setting device handles required by the control, initializing toolbars, performing logons, etc. A DisplayDocument method commands the display control to display the requested document using the document number. It also performs any needed querying or setup required by the control. Conventional document navigation methods are also provided and tell Image Display control to view different parts or pages of the current document. These functions include NextPage, PreviousPage, DisplayMagnifier, AddAnnotation, AddMarginNote, etc. Each of these methods can be implemented with conventional methods, assuming that the appropriate server connections, etc. have been made during the Initialize( ) or DisplayDocument( ) calls.

The Deficiency object represents what is deficient about a given chart or document. Charts may have missing document deficiencies. Documents may have signature, diagnosis, or other deficiencies. Deficiencies are accepted or rejected by physicians and may include free form comment text. Document deficiencies must retain their physical location on a document image. The Deficiency object may be used by the existing application 64 to enable deficiency processing with it's own user interface.

Deficiency Object attributes include Chart which is a reference to the Chart object that contains the deficiency. A Document attribute provides a reference to the Document object that contains the deficiency. If the deficiency is a chart deficiency, this may be null. A DeficiencyType attribute indicates the type of the deficiency, currently either DocumentDeficiency or ChartDeficiency. An AssignedPhysician attribute includes the identifier (ID) of the physician who is assigned to complete this deficiency. Information about the physician is located in a PDMS physician table. A Comments attribute holds the text of the status of the deficiency. Before the comment attribute is completed, it could contain the status "Document xxx missing", "Dictation required," etc. After completion, this attribute could include the status "Signed by Chris", "Dictation recorded," etc. If the deficiency is rejected, the attribute could contain a status of "Not my patient." A LocationOfDeficiency attribute indicates the location of the deficiency on the document, if this is a document deficiency.

Deficiency Object methods include a Complete method which completes the deficiency by using conventional field update techniques with the document management system. A Reject method rejects the deficiency by updating the status field within the document management system. A New method creates a new deficiency in the PDMS by adding new comments and indicating the location of the deficiency. A Delete method deletes an existing deficiency in the PDMS using conventional methods. All information about the particular deficiency is deleted. For example, for a missing document deficiency if the missing document is supplied, there is no reason to keep a record of the deficiency and the deficiency can be deleted. A Reassign method reassigns a deficiency to another physician by updating the assignment attribute. This method also keeps a record of the previously assigned physician. This method checks to see if the user is authorized by checking the permissions table before the reassignment is allowed.

Figure 10:
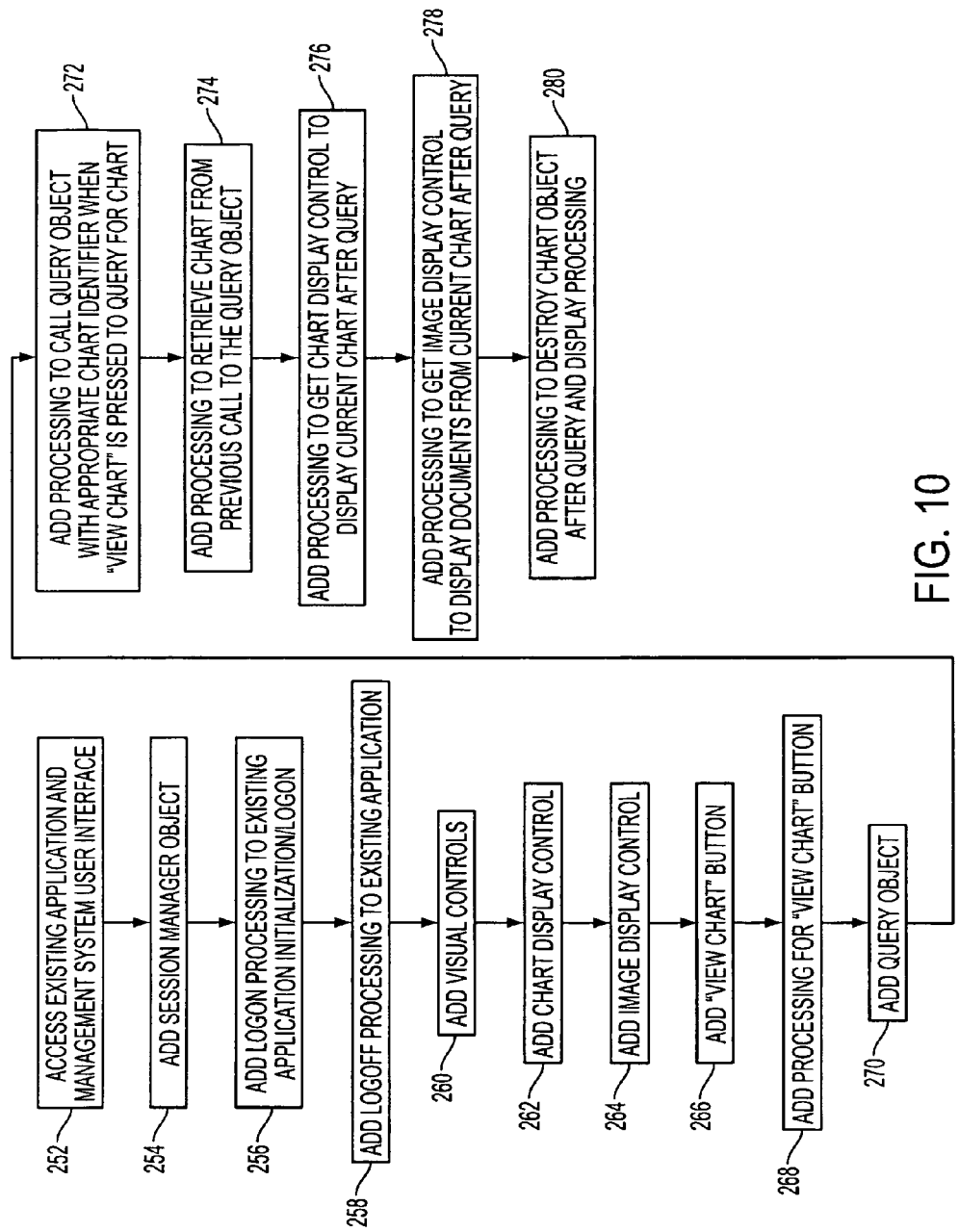
FIG. 10 illustrates a process of the present invention.
Figure 11:
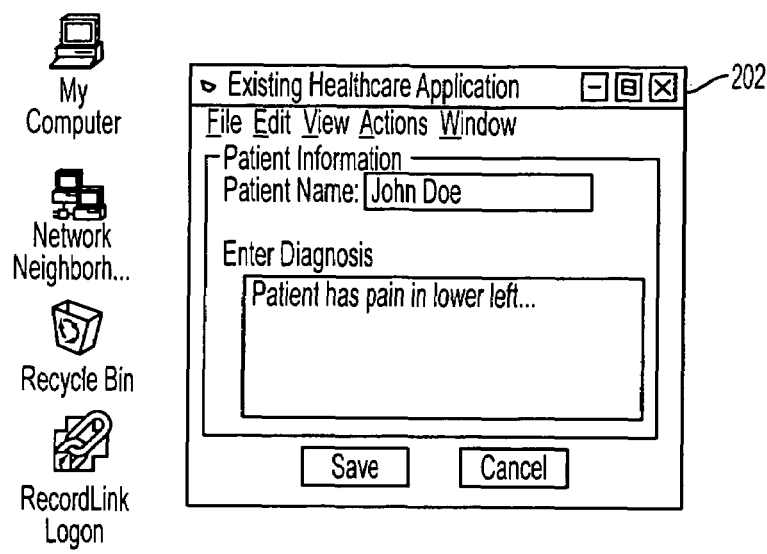
FIG. 11 shows separate interfaces.
Figure 11:
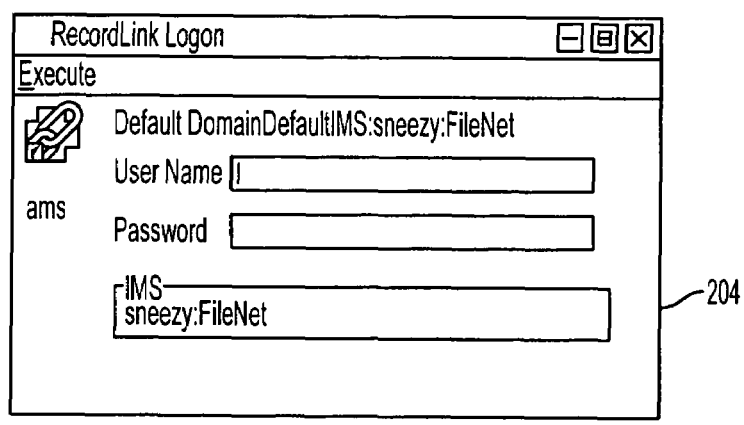
Figure 12:
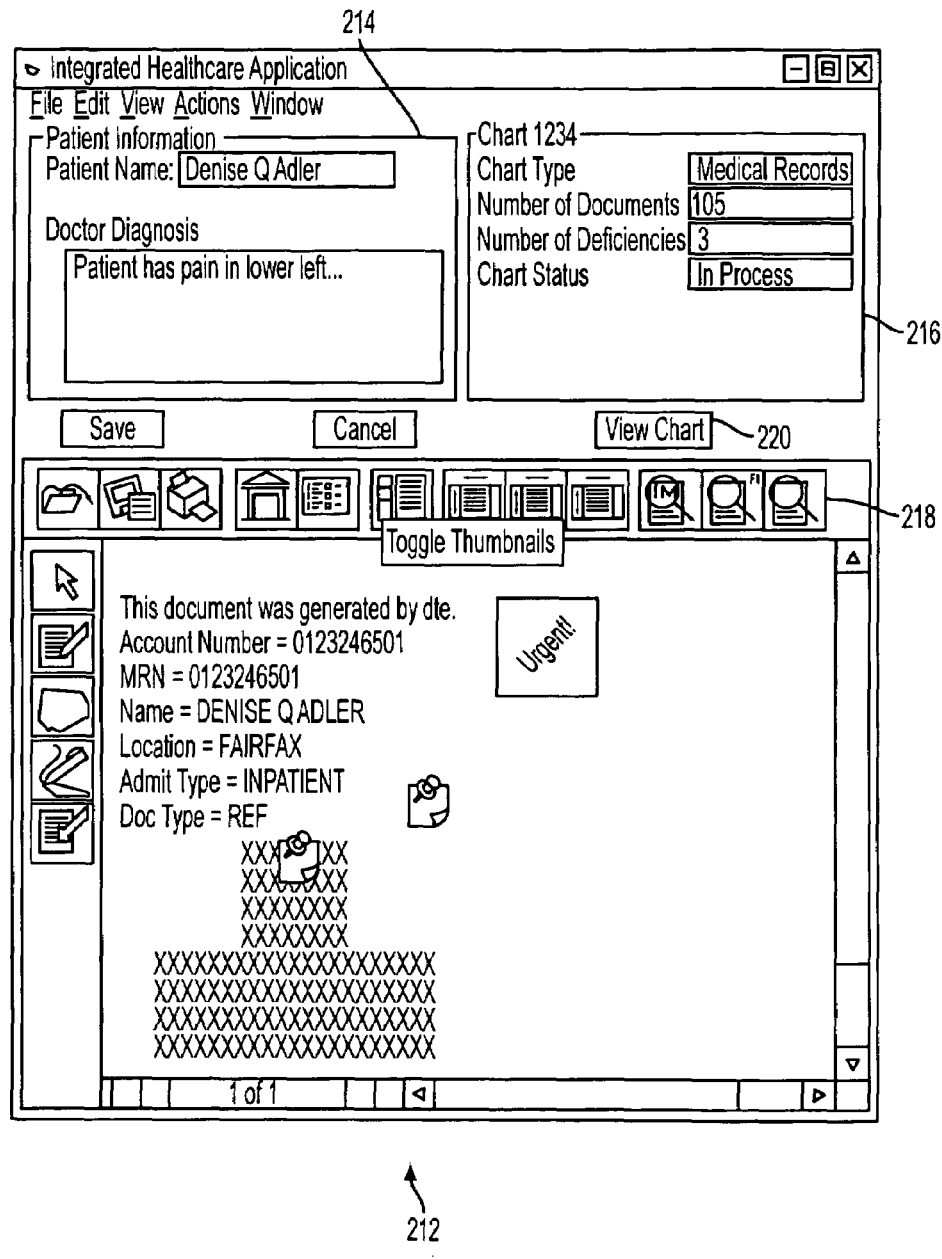
FIG. 12 illustrates an integrated interface.

The process of creating and executing an integrated user interface, as depicted in FIG. 10, starts with accessing 252 the existing application 62 and an existing document management system, such as the AMS RecordLink® system 68. FIG. 11 illustrates the computer desktop that a typical healthcare worker might have today. The regular healthcare application appears in one window 202. This is the main window where the worker does their daily work. Any time that user needs to view patient document images for the patient they are working on, they access the Patient Document Management system (PDMS) in a second window 204, query for the patient they are working on, and then view the chart and related images. The fact that the systems are completely separate slows down the work and introduces the opportunity for error. FIG. 12 illustrates the integrated user interface 212 created using by the present invention. The user interface 212 includes a control 214 provided by the existing application and controls to be added to integrate the existing document management system into the interface 212.

To create the integration interface 62 and accompanying user interface 212 the next operation is to add 254 a SessionManager object to the initialization/logon of the existing application 64. Log-on processing 256 is added where the existing application 64 validates the users user ID and password in the existing system; the same user ID and password could be used to log-on to with the SessionManager object. The log-off processing 258 through the SessionManager object is added where the existing application performs it's shutdown operations (i.e. releasing session handles to databases and other shared resources utilizing conventional methods)

Next, the following three visual controls are added 260 to the part of the existing application's user interface that would normally display information about a single patient (202 in FIG. 11).

First, a ChartDisplay control, myChartDisplay, is added 262 to the existing application's user interface 214 (this is the box labeled by the control as "Chart 1234" in FIG. 12). This operation must initialize the control by setting myChartDisplay.DisplayFields="'ChartType', 'NumberOfDocuments', 'NumberOfDeficiencies', 'ChartStatus'", setting myChartDisplay.EditableFields=ChartType, setting myChartDisplay.Visible=True and setting myChartDisplay.CurrentChart=Nothing. This control 1216 shown in 216 in FIG. 12 and is used in operations below.

Then, an ImageDisplay control, myImageDisplay, is added 264 to the existing application's user interface 214. This operation initializes the control by setting myImageDisplay.CurrentDocument=Nothing, setting myImageDisplay.DisplayButtons to the desired toolbar buttons and calling myImageDisplay.Initialize( ). This control 218 is shown in FIG. 12 and is used in operations below.

Last, a standard command button 220 (see FIG. 12) is added 266 to the existing application. This button is placed on the existing application's form, and is labeled "View Chart." Code is written in the existing application to execute the following operations in the event that this button is pressed. First, create a Query object 270, myQuery, is performed. Next, a query for the active account in the existing application is made 272 by calling the QueryForCharts method of the myQuery object with these parameters: "AccountNumber=1234 (or the account number currently being worked in the existing application)", ", myCharts, 1, myQueryNumber, myMore. The outcome of the query should result in a single chart object in myCharts where that chart is obtained or gotten 274 by setting myChart=myCharts(1). Then, to display the chart in the ChartDisplay control 276, an operation is performed which sets myChartDisplay.CurrentChart=myChart which sets the retrieved chart into the ChartDisplay control and a call to myChartDisplay.Refresh( ) is performed. The Chart Display control 216, as a result, displays the desired chart. Then, the Image Display control is set up 278 by sending it the first document in the chart: myImageDisplay.DisplayDocument(myChart.ChartDocuments(1)) which displays that first document. Finally, the Query object contained in myQuery and the Chart object in MyCharts are eliminated since they are no longer needed 280.

The present invention provides a healthcare specific document imaging application program interface (API) that can easily be integrated into an existing healthcare application. The API allows simple and direct access to a typical Patient Document Management system (particularly to existing systems, such as the AMS AccountLink and/or RecordLink® systems). The invention specifically targets the needs of healthcare organizations and applications. The functional improvements and benefits would include improved security, user authorization, user authentication, patient chart deficiency processing and auditing.

The present invention has been described with respect to providing chart and document viewing and editing and chart deficiency completion. It is also possible to provide chart analysis and chart coding modules. The set of objects and controls described herein could be enhanced to provide additional functionality as discussed below. The ImageDisplay control could be modified to display/present full motion video, audio clips, diagnostic quality images or modified to allow native document display and document editing. For example, if a document was originally created in Microsoft Word, embed Microsoft Word inside the ImageDisplay control so Word renders the document, and even allow editing and storage of the document. This enhancement could support Microsoft Word, Microsoft Excel, or a third party physician transcription system. This functionality would be transparent to the existing healthcare application. The Query object could be modified to query for charts or documents across multiple document management systems and the SessionManager could be modified to handle sessions with these systems. This functionality would be transparent to the existing healthcare application. The Query object could be modified to query for charts or document across disparate information systems and current ChartDisplay, DocumentDisplay, and ImageDisplay controls could be modified to display this disparate information; modify current SessionManager to handle sessions with these systems. This functionality would also be transparent to the existing healthcare application. The Deficiency object could be modified to allow voice dictation for deficiency completion/rejection process. Deficiency object could also be modified to utilize native document display noted above to allow editing of deficient documents by physicians. The DocumentDisplay control can be modified to allow copying a document from one chart to another (which could also be accomplished by adding additional methods to the Document object) and this functionality could be provided through the API set to the existing healthcare application. The Document object can be modified to retrieve actual data from an image document. For example, if a document image displays a patient's name, account number, and diagnosis, provide a means to read the diagnosis from the document and return it to the existing healthcare application. This enhancement may utilize ICR and/or OCR, or extract the data from conventional a data representation. These methods could be provided in the API set so the existing healthcare application may utilize this functionality. The objects and controls could be implemented in Java to broaden the compatibility of the API with existing healthcare applications. The architecture of the controls and objects could be modified to make use of a middle tier. This tier could better utilize processing and storage resources, and would provide conventional benefits of a three-tier architecture (connection pooling, application roll-out and distribution, simplified administration, etc). Additionally, an additional set of objects could be provided which would the existing healthcare application manage version control and application distribution/roll-out.

The many features and advantages of the invention are apparent from the detailed specification and, thus, it is intended by the appended claims to cover all such features and advantages of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

The invention claimed is:

1. A method of using an Application Programming Interface (API) to enable a healthcare system (HCS)—executed and used by healthcare workers for viewing healthcare records managed by the HCS—to access a document management system (DMS) server managing patient documents and making them available for access by plural user terminals, the API providing authorization and access to the DMS server, the method comprising:

adding a user interface control to a pre-existing user interface of the HCS by adding to the HCS code for executing functions or methods of the user interface control and the API, thereby creating a modified HCS, where the user interface control is part of or interfaces with the API;

interactively logging onto the modified HCS by executing an HCS user authentication process of the HCS which is separate from the API;

based on authentication information related to the HCS user authentication process, automatically authenticating a user to use the DMS server;

after authenticating the user to the DMS server, receiving interactive input by the user interacting with the user interface control to cause the API to submit to the DMS server a request to locate a document managed at the DMS server; and displaying the requested document based on a response from the DMS server and navigating the requested document from within the modified HCS using the user interface control.

2. A method according to claim 1, wherein the interacting causes the user interface control to access a control object of the API that performs the submitting.

3. A method according to claim 2, wherein the control object is a query control object.

4. A method according to claim 1, further comprising adding a user interface element to the HCS by adding code to the HCS, where the user interface element performs the displaying and navigating of the requested document.

5. A method as recited in claim 1, wherein the interactive logging onto the modified HCS comprises a healthcare worker providing log-on information to the modified HCS using the user interface of the HCS, and wherein the automatically authenticating to the DMS comprises the API automatically logging the user to the document management system using the log-on information from the user interface.

6. A method as recited in claim 1, wherein the interactive logging onto the modified HCS comprises a healthcare worker providing log-on information to the modified HCS using the user interface of the HCS, and wherein the automatically authenticating to the DMS comprises the API automatically logging the user onto the document management system using the log-on information from the user interface.

7. A method as recited in claim 1, wherein accessing, displaying, and navigating the requested document is based on access and security privileges of a user obtained by the authenticating with the HCS or the DMS server.

8. A method as recited in claim 1 further comprising performing chart deficiency completion from the user interface.

9. A method as recited in claim 1, further comprising displaying and editing of fields with the requested document based on access and security privileges of a user obtained by the authenticating with the HCS or the DMS server.

* * * * *

UNITED STATES PATENT AND TRADEMARK OFFICE
CERTIFICATE OF CORRECTION

PATENT NO. : 7,590,617 B1
APPLICATION NO. : 09/366749
DATED : September 15, 2009
INVENTOR(S) : Christopher T. Voigt et al.

It is certified that error appears in the above-identified patent and that said Letters Patent is hereby corrected as shown below:

Title Page, Item (57) (Abstract), Line 1, change "desk top" to --desktop--.
Column 7, Line 31, after "BackgroundColor" insert --,--.
Column 10, Line 49, after "methods)" insert --.--.

Signed and Sealed this

First Day of December, 2009

David J. Kappos
*Director of the United States Patent and Trademark Office*